(12) United States Patent
Rasmussen

(10) Patent No.: US 9,149,284 B2
(45) Date of Patent: *Oct. 6, 2015

(54) SYSTEMS AND METHODS FOR PROVIDING A BONE MILLING DEVICE

(71) Applicant: G. Lynn Rasmussen, Salt Lake City, UT (US)

(72) Inventor: G. Lynn Rasmussen, Salt Lake City, UT (US)

(*) Notice: Subject to any disclaimer, the term of this patent is extended or adjusted under 35 U.S.C. 154(b) by 202 days.

This patent is subject to a terminal disclaimer.

(21) Appl. No.: 13/726,386

(22) Filed: Dec. 24, 2012

(65) Prior Publication Data

US 2014/0012262 A1 Jan. 9, 2014

Related U.S. Application Data

(63) Continuation of application No. 12/191,217, filed on Aug. 13, 2008, now Pat. No. 8,337,498.

(51) Int. Cl.
*A61B 17/00* (2006.01)
*A61B 17/16* (2006.01)
*A61B 17/15* (2006.01)
*A61B 17/17* (2006.01)

(52) U.S. Cl.
CPC .......... *A61B 17/1675* (2013.01); *A61B 17/157* (2013.01); *A61B 17/1764* (2013.01)

(58) Field of Classification Search
CPC .......... A61B 17/1666; A61B 17/1668; A61B 17/1675

USPC ....................................... 606/79–85
See application file for complete search history.

(56) References Cited

U.S. PATENT DOCUMENTS

| 5,336,226 | A | 8/1994 | McDaniel et al. |
| 5,403,320 | A | 4/1995 | Luman et al. |
| 5,432,367 | A | 7/1995 | Hoshiko et al. |
| 5,766,261 | A | 6/1998 | Neal et al. |
| 5,782,922 | A * | 7/1998 | Vandewalle ............ 606/87 |
| 6,045,302 | A | 4/2000 | Orr |
| 6,162,227 | A | 12/2000 | Eckhardt et al. |
| 6,874,978 | B2 | 4/2005 | Gongola |
| 7,326,214 | B2 | 2/2008 | Michelson |
| 8,337,498 | B2 | 12/2012 | Rasmussen |
| 2004/0193175 | A1 | 9/2004 | Maroney et al. |
| 2006/0015111 | A1 | 1/2006 | Fenton |

FOREIGN PATENT DOCUMENTS

| WO | WO 2008/037984 A2 | 4/2008 |
| WO | WO 2010/019284 A1 | 2/2010 |

* cited by examiner

*Primary Examiner* — Nicholas Woodall
(74) *Attorney, Agent, or Firm* — Kirton McConkie; David B. Tingey

(57) ABSTRACT

A milling tool system for accurately preparing a portion of the tibia preparatory to making femoral resections. The milling tool system provides a minimally invasive procedure to provide an aperture within an exposed surface of the tibia, the aperture then being used as a referencing surface to accurately resect the femur. Once the femur resections have been made, the remaining uncut portions of the tibia are exposed and easily accessible for the tibial resections.

20 Claims, 10 Drawing Sheets

SYSTEMS AND METHODS FOR PROVIDING A BONE MILLING DEVICE

RELATED APPLICATIONS

This application is a continuation of U.S. patent application Ser. No. 12/191,217 filed Aug. 13, 2008, entitled "SYSTEMS AND METHODS FOR PROVIDING A BONE MILLING DEVICE", which is incorporated herein by reference in its entirety.

BACKGROUND OF THE INVENTION

1. Field of the Invention

The present invention is related to the use of instruments for guiding preparation of a knee for resection, as well as for guiding preparation of a knee for installation of an implant during an arthroplasty procedure. In particular, the present invention is related to a system for guiding a milling tool along a specific axis to provide an aperture of a desired depth, prior to resection.

2. Background and Related Art

During a knee arthroplasty, a surgeon typically must gain access to the knee joint in order to perform resections of existing bone and cartilage so as to shape the tibia and femur to fit mating surfaces of the implant. This shaping is initiated by making resection cuts to the knee joint either by referencing off the femur or off the tibia. The accuracy and precision of the resection cuts greatly affects the quality of the arthroplasty procedure. Therefore, extreme caution is used in planning executing the resection cuts based on the chosen reference.

Femoral cuts are typically easier to make in surgery because the femur is easily exposed and accessible. Also, many techniques exist to open the knee and expose the femur in a relatively non-invasive manner. Once the femoral cuts have been made, the tibia is better exposed and accessible for the tibial cuts.

While preparing the femur first is more convenient and relatively non-invasive, ideal femoral cuts are referenced off a prepared tibia. However, complete preparation of the tibia is hindered by overlapping portions of the femur. With the knee in flexion, there is always access to the central part of the tibia; however this exposure is insufficient to completely prepare the tibia.

It would therefore be advantageous to have instrumentation for sufficiently preparing the tibia for use as a reference to make the femoral resections. It would be further advantageous if the instrumentation was capable of interchangeable use with other necessary instrumentation. Finally, it would be advantageous to have instrumentation that could access and sufficiently prepare the tibia in a relatively non-evasive manner.

SUMMARY OF THE INVENTION

The present invention is related to the use of instruments for guiding preparation of a knee for resection, as well as for guiding preparation of a knee for installation of an implant during an arthroplasty. In particular, the present invention is related to a system for guiding a milling tool along a specific axis to provide an aperture of a desired depth, prior to resection.

An implementation of the present invention includes a bone milling system having a milling tool member and a guide rod. The guide rod is partially deposited within the intramedullary (IM) canal of the bone, and a portion of the guide rod extends outwardly from the IM canal along a desired axis. The exposed portion of the guide rod is adapted to rotatably insert within a cavity of the milling tool member. As such, the milling tool member is guided along the desired axis by the exposed portion of the guide rod.

The milling tool member includes a cutting head portion and a shaft. The cutting head portion includes a blade having a cutting edge and a window. The cutting edge cuts the aperture into the bone, and the window provides an escape route for the removed bits of bone debris. A cavity is also provided running through the shaft and cutting head portion. The cavity is generally tube shaped having an open end and a closed end. The open end is in fluid communication with an opening in the blade. The closed end includes a shank for coupling the milling tool member to a drill or other device for rotating the member.

Following creation of the aperture, a resection block is combined with the bone milling system to resect the bone. In some embodiments, the aperture is first made in the tibia and then used as a reference point and/or mounting surface for tensioning the knee and making resections to the exposed femur. In other embodiments, the aperture is first made in the tibia and then used as a reference point and/or mounting surface for positioning a resection block to resect the tibia. Other embodiments of the present invention include a bone milling device that incorporates a guide rod, a cutting surface and a shank into a singular unit.

While the methods and processes of the present invention have proven to be particularly useful in the area orthopedics, those skilled in the art can appreciate that the methods and processes can be used in a variety of different applications and in a variety of different areas of manufacture to yield functionally equivalent results.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE INVENTION

The present invention is related to the use of instruments for guiding preparation of a knee for resection, as well as for guiding preparation of a knee for installation of an implant during an arthroplasty. In particular, the present invention is related to a system for guiding a milling tool along a specific axis to provide an aperture of a desired depth.

Figure 1:
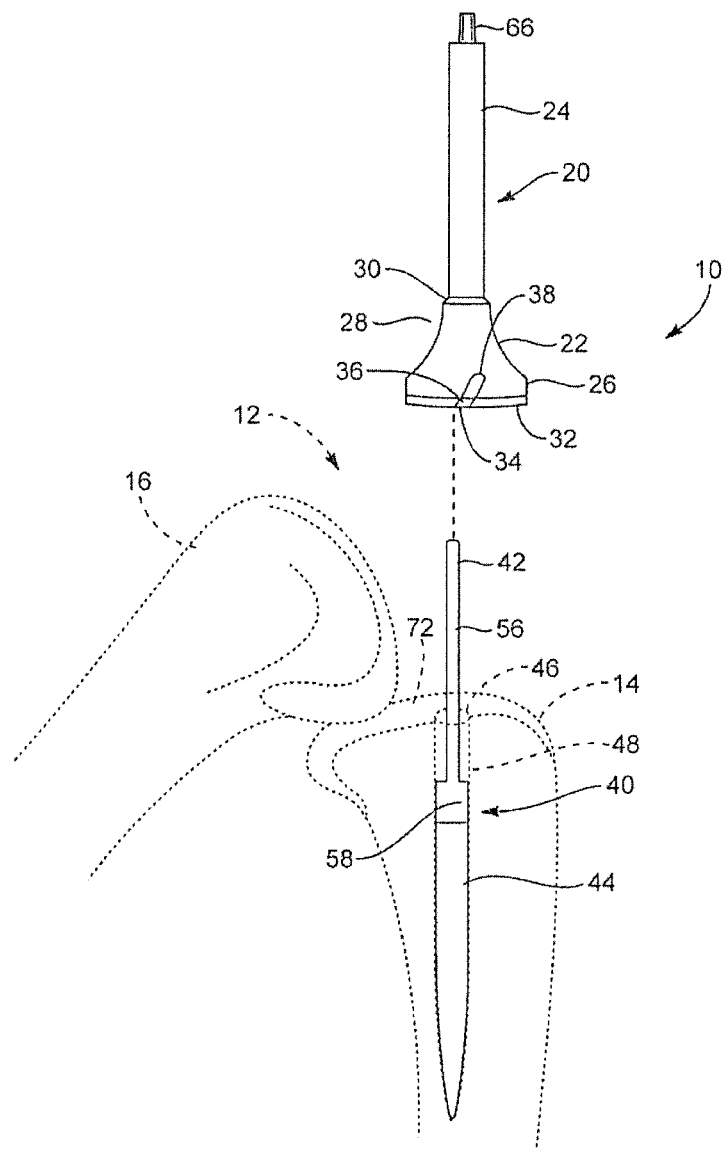
FIG. 1 is a perspective view of a representative embodiment of the present system as incorporated into a knee, shown in phantom.

Referring now to FIG. 1, a perspective view of an implementation of the current invention is shown as positioned within a knee 12 in flexion, shown in phantom. The bone milling device 10 comprises a milling bit 20 and a guide rod 40. The bone milling device 10 generally comprises surgical metal materials that are compatible with surgical applications, such as surgical steel, titanium, aluminum, and alloys thereof. However, one of skill in the art will appreciate that other non-metallic materials, such as Teflon and nylon, may be incorporated into the current invention within the scope of the present disclosure. For example, in one embodiment a Teflon coating is applied to opposing surfaces of the bone milling device 10 to reduce friction.

Figure 2:
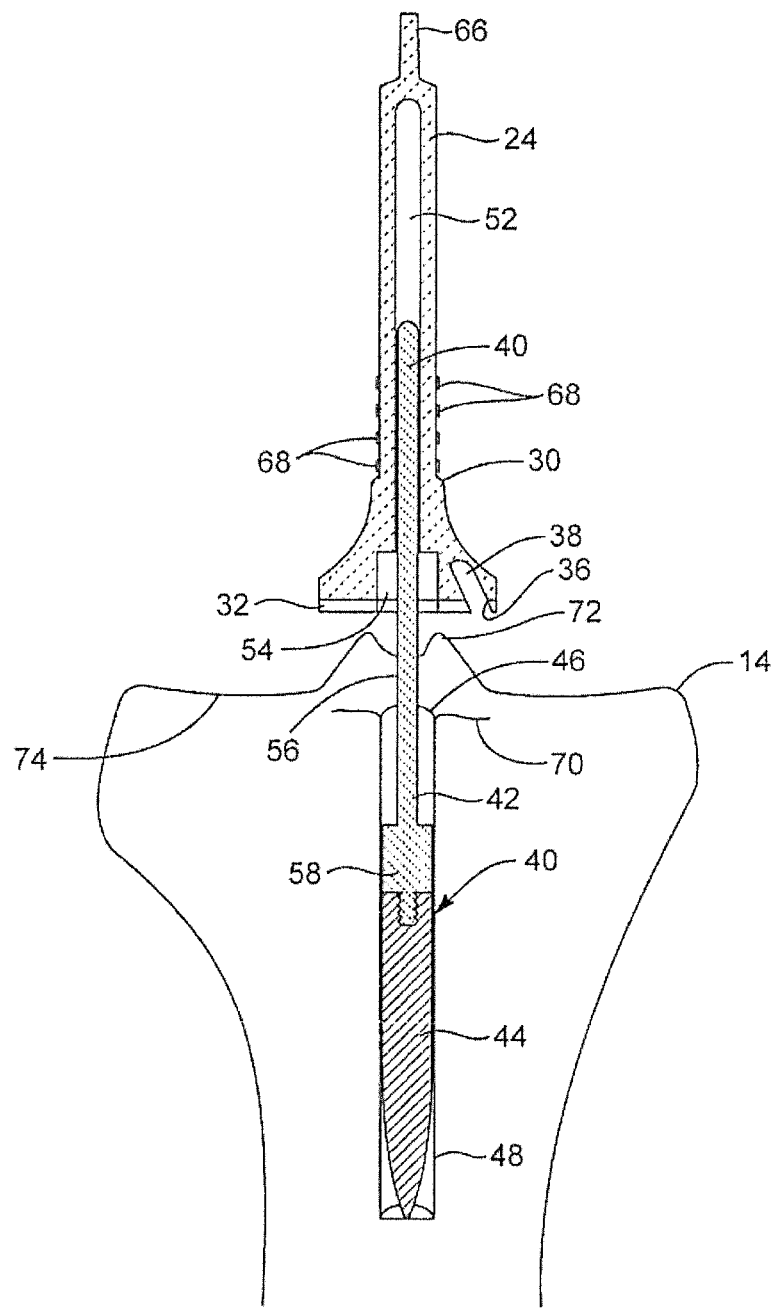
FIG. 2 is a cross-sectioned view of a representative embodiment of the present system prior to formation of an aperture.
Figure 3:
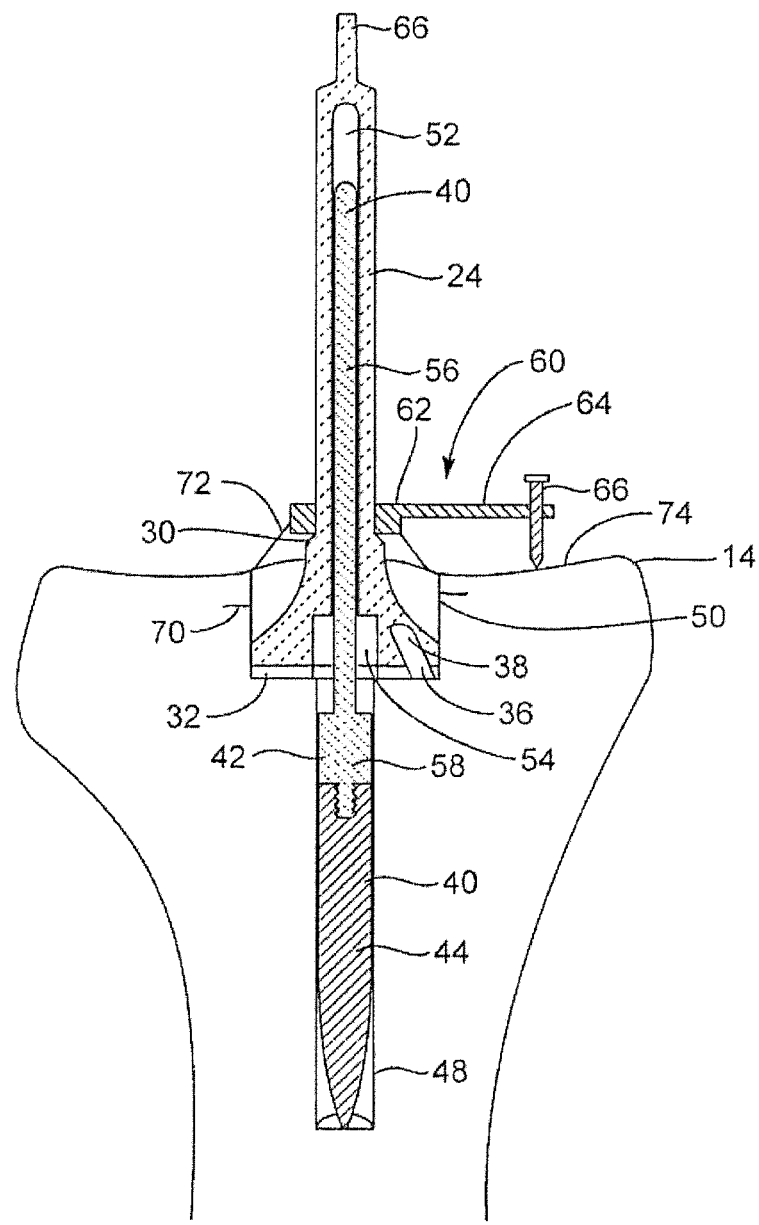
FIG. 3 is a cross-sectioned view of a representative embodiment of the present system following formation of an aperture, demonstrating use of a depth gauge.

Referring now to FIGS. 1-3, the milling bit 20 comprises a cutting head portion 22 and a shaft portion 24. The cutting head portion 22 is generally bell-shaped having a wider base 26 and a narrower, tapered top 28 that joins the shaft portion 24. In some implementations of the current invention, a ledge or stepped surface 30 is interposed between the cutting head portion 22 and the shaft portion 24 to support a depth gauge 60, as shown in FIG. 3. The shaft portion 24 further comprises a shank 66 for coupling the milling bit 20 to a drill or other device for rotating the bit 20.

The cutting head portion 22 further comprises a removable blade 32. The removable blade 32 is generally disk shaped having a cutting edge 34 and a window 36. The cutting edge 34 is provided to cut through the bone to create the aperture 50, while the window 36 is provided to remove the cut bone debris from the aperture 50. In this manner, the aperture 50 is both cut and cleared by the milling bit 20. The cutting head portion 22 further includes a window 38 that aligns with the window 36 of the removable blade 32. As such, bone debris is entirely removed from the cutting head portion 22 of the milling bit 20 and does not interfere with the ability of the milling bit 20 to form the aperture 50.

The milling bit 20 further comprises a cavity 52 extending through the central core of the shaft portion 24 and the cutting head portion 22. The cavity 52 is closed on one end and includes an opening 54 in the cutting head portion 22 of the bit 20. The cavity 52 comprises a diameter that is adapted to rotatably receive a portion of the guide rod 40. The tolerance between the cavity 52 and the guide rod 40 permits the bit 20 to freely rotate around the guide rod 40 yet controls and limits the movement of the bit 20 relative to the axis of the guide rod 40. As such, the interaction between the cavity 52 and the guide rod 40 ensures that the angle of the aperture 50 is parallel to the angle of the guide rod 40. The guide rod 40 is inserted or anchored within a portion of the bone 14 that is to receive the aperture 50. Typically, the bone 14 is predrilled to provide an access or opening 46 into the intramedullary (IM) canal 48 of the bone. The pre-drilling procedure is common to the area of orthopedic medicine. Following this procedure, a first end 44 of the guide rod 40 is inserted into the opening 46 and positioned within the IM canal 48 such that a portion of the second end 42 of the guide rod 40 extends outwardly from the opening 46.

In one embodiment, the first and second ends 44 and 42 of the guide rod 40 are threadedly coupled to form the guide rod 40. As such, the first end 44 of the guide rod 40 may threadedly receive a plurality of compatible surgical devices. For example, in one embodiment the second end 42 of the guide rod 40 is removed, following creation of the aperture 50, and replaced with another surgical instrument needed to complete the arthroplasty procedure.

The second half 42 of the guide rod 40 comprises a post portion 56 and a base 58. The base 58 is threadedly coupled to the first end 44 and generally comprises the same diameter as the first end 44. The post portion 56 extends outwardly from the base 58 and is substantially positioned exterior to the IM canal 48. As previously discussed, the diameter of the post portion 56 is selected and adapted to rotatably insert within the cavity 52 of the milling bit 20. In one embodiment the diameter of the base 58 is made greater than the diameter of the post portion 56 so as to increase the surface area of the guide rod 40 in contact with the IM canal, yet still provide the post portion 56 with a diameter compatible with the cavity 52. In another embodiment, the base 58 and the first end 44 further include fluted outer surfaces to enhance contact with the IM canal 48 and prevent rotation of the guide rod 40 within the IM canal 48.

The depth and positioning of the guide rod 40 within the IM canal is selected to permit the milling bit 20 to precisely cut the aperture 50 to a desired depth. The accuracy of the depth of the aperture 50 is a crucial element of any arthroplasty procedure. As such, the milling device 10 further comprises means for accurately determining the depth of the aperture 50. For example, in one embodiment the outer surface of the shaft portion 24 comprises a plurality of annular reference marks 68. The reference marks 68 provide a visual indication of the depth of the removable blade 32 relative to various physiological references on the bone being cut. In an embodiment where the aperture 50 is being cut into the tibia 14, the required depth of the aperture 50 is either 2 mm below the normal level 70 of the bone, 13 mm below the tibial spines 72, or 10 mm below the lateral side 74. Thus, the reference marks 68 are observed relative to the physiological references 70, 72 and 74 to determine the depth of the aperture 50. Where the aperture is being cut into another bone, such as the femur 16, other boney references are used, as known in the art.

In another embodiment, a depth gauge 60 is placed over the shaft portion 24 of the bit 20 and supported by the stepped surface 30. The depth gauge 60 includes a base 62, an arm 64 and a pin 66. The base 62 further includes an aperture having a diameter to rotatably receive the shaft portion 24 of the bit 20. The arm 64 extends outwardly from the base 62 so as to position the pin 66 beyond the aperture 50. In one embodiment, the arm 64 further comprises a joint to adjust the length of the arm 64. In another embodiment, the arm 64 further comprises a set screw to adjust and lock the pin 66 to a desired position relative to the arm 64. In yet another embodiment, a plurality of depth gauges 60 is provided to accommodate various physiological references on the bone being cut.

The depth gauge 60 provides a physical indication of the depth of the removable blade 32 relative to the various physiological references, as previously discussed. In one embodiment, the depth gauge 60 is seated against the stepped surface 30 and the arm 64 and the pin 66 are adjusted to be in alignment with the desired physiological reference 74. Additionally, the height of the pin 66 is set relative to the physiological reference to produce an aperture 50 of a desired depth. Thereafter, the depth gauge 60 is held in place and prevented from rotating while the bit 20 is rotated to form the aperture 50. Once the pin 66 touches the physiological reference 74, the bit 20 is removed from the aperture 50, having achieved the desired depth.

Figure 4:
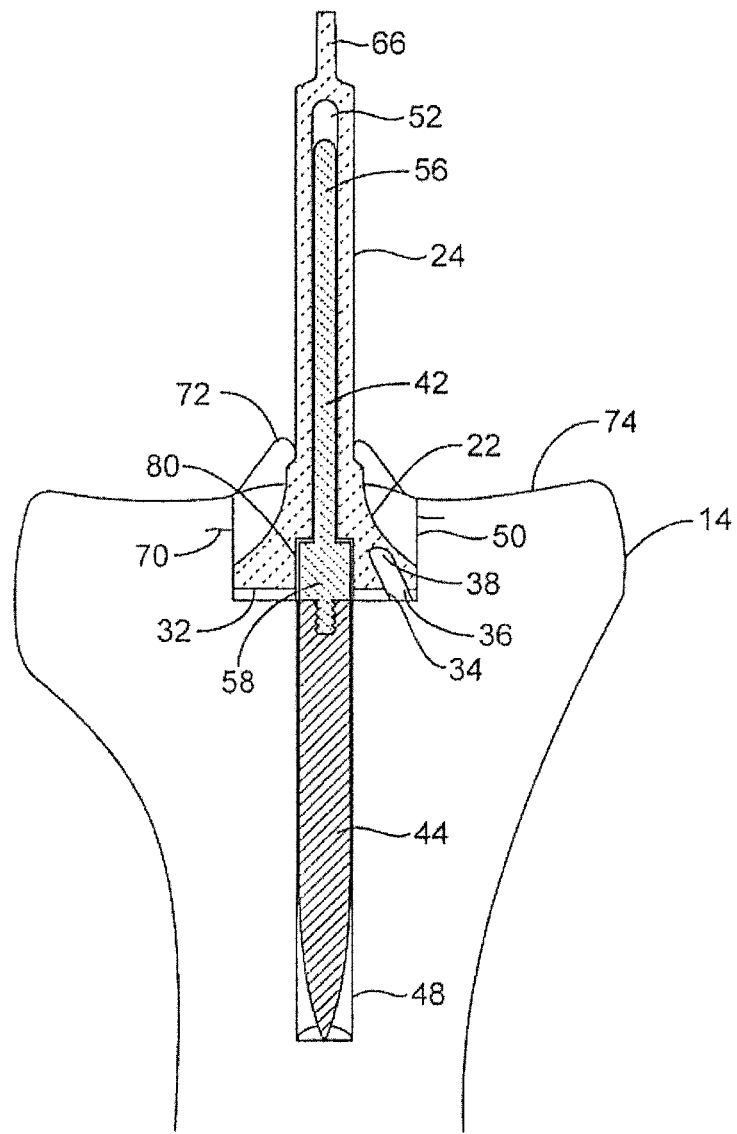
FIG. 4 is a cross-sectioned view of a representative embodiment of the present system following formation of an aperture.

Referring now to FIG. 4, another method for accurately cutting the aperture 50 to a desired depth is shown. In this method, the desired aperture 50 depth is attained by cutting into the bone 14 until the cutting bit 20 contacts the base 58 of the guide rod 40. This method requires that the base 58 of the guide rod 40 be accurately positioned within the IM canal 48 relative to the cutting edge 34 of the blade 32. Therefore, the blade 32 cuts and descends into the bone 14 along the guide rod 40 until the point at which the cutting head 22 contacts the base 58. Once contact between the cutting head 22 and the base 58 occurs the milling bit 20 is removed from the aperture 50. In one embodiment, the cutting head portion 22 of the milling bit comprises a recessed compartment 80 having a diameter adapted to compatibly and rotatably receive the base 58 of the post portion 56. Thus, in this embodiment the depth of the base 58 is set within the IM canal 48 such that when the base 58 fully engages the recessed compartment 80, the cutting edge 34 of the blade 32 is positioned accurately at the desired depth of the aperture 50. While several different methods have been discussed, one of skill in the art will appreciate that various other methods and apparatuses may be successfully combined with the milling device 10 to achieve the desired results.

Figure 5:
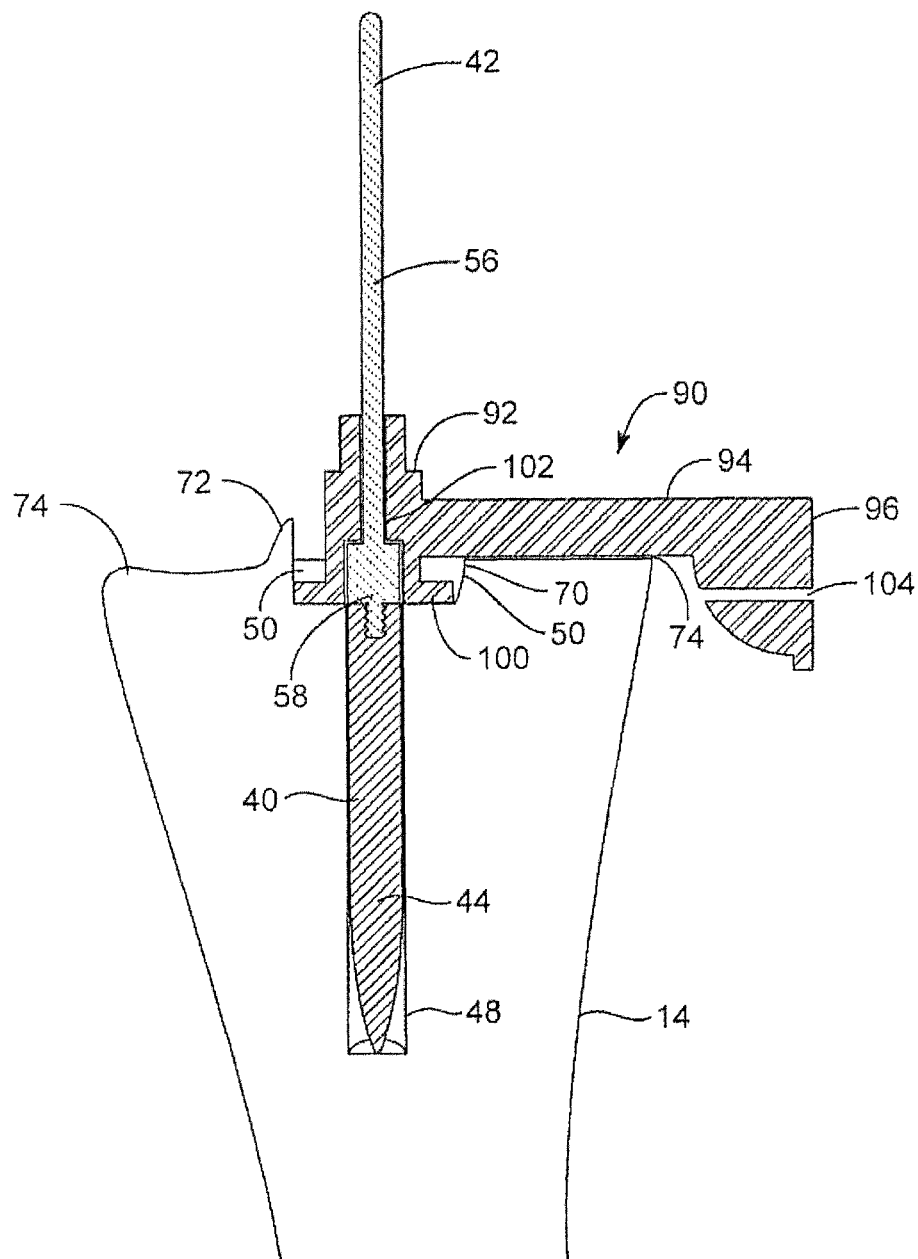
FIG. 5 is a cross-sectioned view of a representative embodiment of the present system incorporating a resection block.

Referring now to FIG. 5, the tibia 14 is shown following formation of the aperture 50 and prior to resection. Once the aperture 50 is provided, the guide rod 40 may be further utilized to assist in completing the arthroplasty procedure. For example, in one embodiment a resection block 90 is positioned over the guide rod 40, via a channel 132, and seated within the aperture 50. The resection block 90 comprises a base 92, an arm 94, and a cutting guide block 96. The base further comprises a flange portion 100 having a diameter equal to the diameter of the aperture 50. Additionally, the base 92 includes a channel 102 having contours and dimensions adapted to compatibly engage the post portion 56 and the base 58 of the guide rod 40. As such, the resection block 90 accurately seats within the aperture 50 and is steadied by the interposing and complimentary surfaces of the guide rod 40.

Figure 5A:
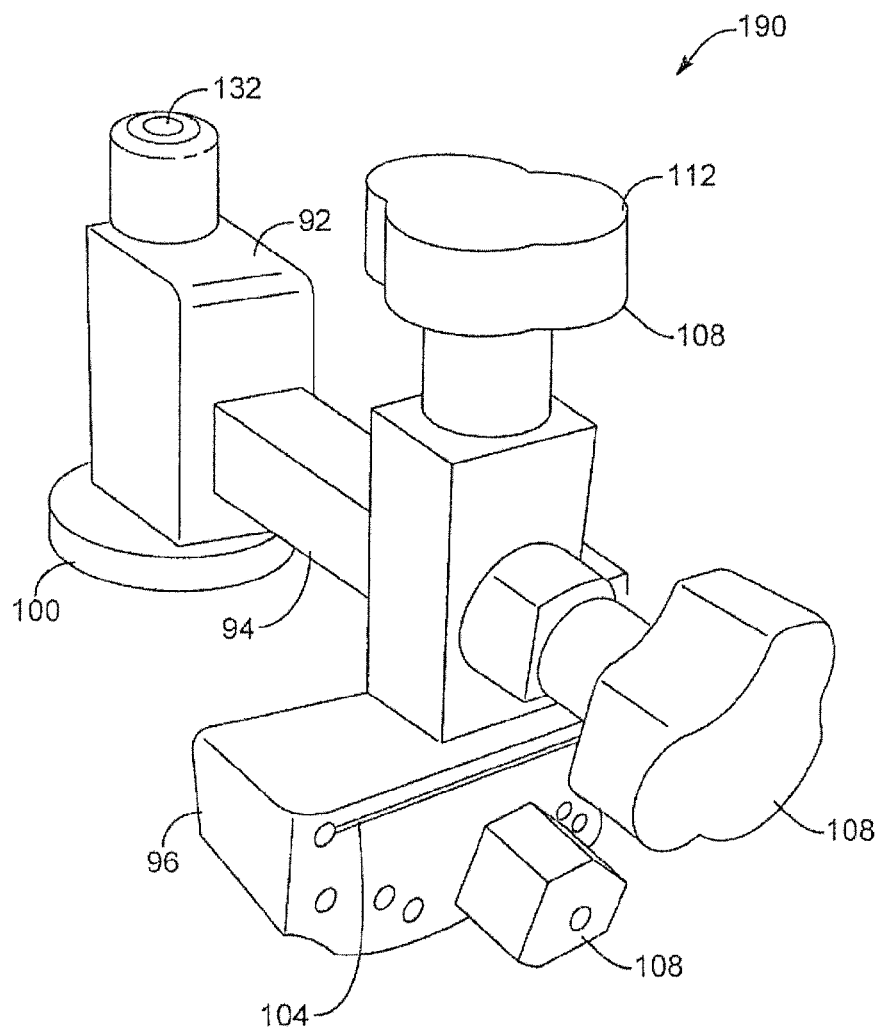
FIG. 5A is a perspective view of a representative embodiment of a resection block having a plurality of adjustments and apertures.

The arm 94 of the resection block 90 is attached to the base 92 at a height equal to the lateral side 74 of the bone 14. As such, the arm 94 clears the surface of the bone 14 and extends laterally from the base 92 beyond the aperture 50. In one embodiment, the resection block 190 further includes a plurality of adjustments 108 to position the arm 94 relative to the depth and location of the aperture 50 as required by the individual, physiological features of the bone 14 undergoing the arthroplasty, as shown in FIG. 5A. Thus, one resection block 90 may be infinitely adjusted and adapted for use with any procedure as required.

The cutting guide block 96 is attached to the end of the arm 94 opposite the base 92. The cutting guide block 96 is positioned such that a saw blade (not shown) may be inserted through the slot 104 to resect the bone 14 to the depth of the aperture 50. In one embodiment, the resection block 90 further includes a plurality of adjustments 112 to position the cutting block guide 96 relative to the depth and location of the aperture 50 as required by the individual, physiological features of the bone portions 70, 72 and 74 undergoing resection, as shown in FIG. 5A. In some implementations of the current invention, the cutting block guide 96 further comprises a plurality of apertures for attaching the cutting block guide 96 to the bone 14 via fasteners. In other implementations, a plurality of adjustments permits removal of the cutting block guide 96 from the arm 94. Therefore, in one embodiment the cutting block guide 96 is first positioned on and attached to the bone 14 with fasteners to ensure accurate positioning. Following attachment, the cutting block guide 96 is then removed from the remainder of the resection block 90 and the resections are made. As such, the resections are made accurately and efficiently with minimal componentry.

In another embodiment, instrumentation for performing the formal cuts is inserted into and/or referenced from the final depth of the aperture 50. Since the depth of the aperture 50 is the final level for the tibial cuts, all femoral cuts may be accurately referenced from the depth of the aperture 50. As such, the aperture 50 provides a sufficient and relatively non-invasive reference point for the tibia 14. Once the femoral cuts are made, the remaining uncut portions of the tibia 14 are then exposed and easily accessible for resection. In another embodiment, tensioning devices are combined with the guide rod 40, the resection block 90, and the aperture 40 to tension the knee 12 as part of the resection procedure. Tensioning devices and procedures as taught in U.S. patent application Ser. No. 11/349,772, entitled GUIDE ASSEMBLY FOR GUIDING CUTS TO A FEMUR AND TIBIA DURING A KNEE ARTHROPLASTY, filed Feb. 8, 2006, may be easily combined with the present device 10, and is incorporated herein by reference, in its entirety. Modifications to the instrumentation and bone 14 are discussed in connection with FIG. 5B, below.

Figure 5B:
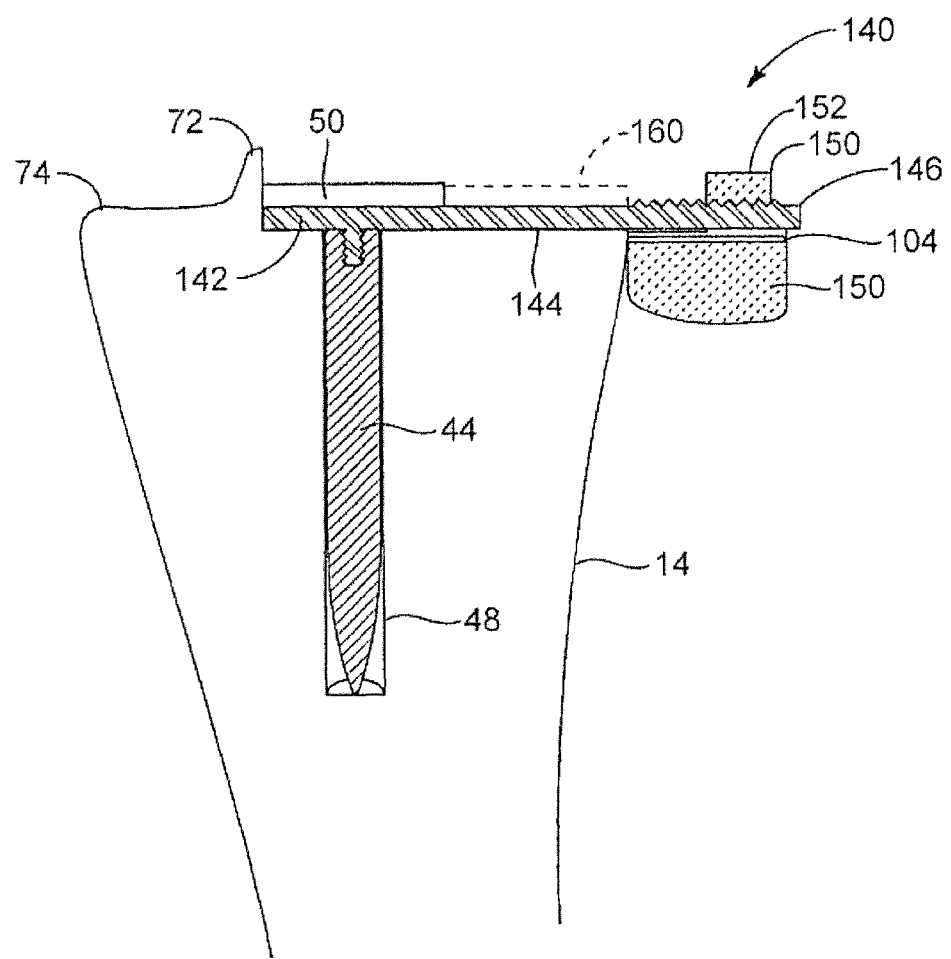
FIG. 5B is a cross-sectioned view of a representative embodiment of a resection block system coupled to a portion of the guide rod.

Referring now to FIG. 5B, an implementation of a resection block is shown as combined with the first end 44 of the guide rod 40. In this embodiment, the post portion or the second end 42 of the guide rod 40 is removed from the first end 44 and replaced with a resection block system 140. The resection block system 140 includes an integrated base 142 and arm 144, as well as a sled-style cutting guide block 150. The base 142 is disk-shaped having a diameter slightly less than the diameter of the aperture 50. The arm 144 extends laterally outward from the base 142 in the same plane as the base 142. As such, a portion 160 of the bone 14 must be removed to provide a pathway for the arm 144. In one embodiment, a rongeur or other surgical device is used to remove the bone portion 160 to create the pathway. Once the bone portion 160 is removed, the first end 44 of the guide rod 40, with the attached system 140, is repositioned within the IM canal 48. The cutting guide block 150 is then slid over the distal end 146 of the arm 144 and positioned against the bone 14. At this point, the cutting guide block 150 is securely attached to the bone via fasteners and the required resections are made via the slot 104. In one embodiment, the cutting guide block 150 further includes means for releasing the guide block 150 from the arm 144 while the guide block 150 is fastened to the bone 14. For example, an upper portion 152 of the guide block 150 may be adapted to be removable thereby releasing the lower, fastened half of the block 150 from the remainder of the system 140.

In an alternate embodiment, the cutting guide block 150 is first slid over the distal end 146 of the arm 144 so that the slot 104 of the guide block 150 aligns with femur 16 rather than with the tibia 14. In this configuration, the guide block 150 is positioned, relative to the depth of the aperture 50, to make the femoral cuts. Thus, the aperture 50 of the tibia 14 acts as a reference point to accurately make the femoral cuts. Once the femoral cuts have been made, the guide block 150 is removed and repositioned to make the tibial cuts, as previously discussed.

Figure 6:
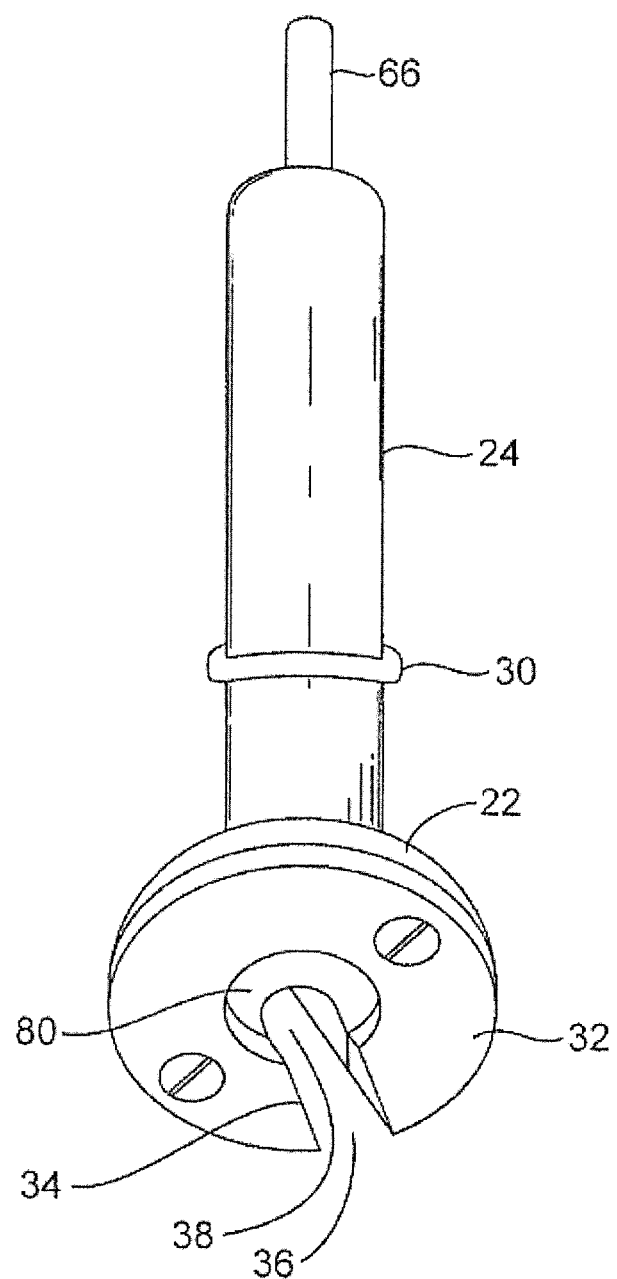
FIG. 6 is a perspective view of a representative embodiment of the milling bit.
Figure 7:
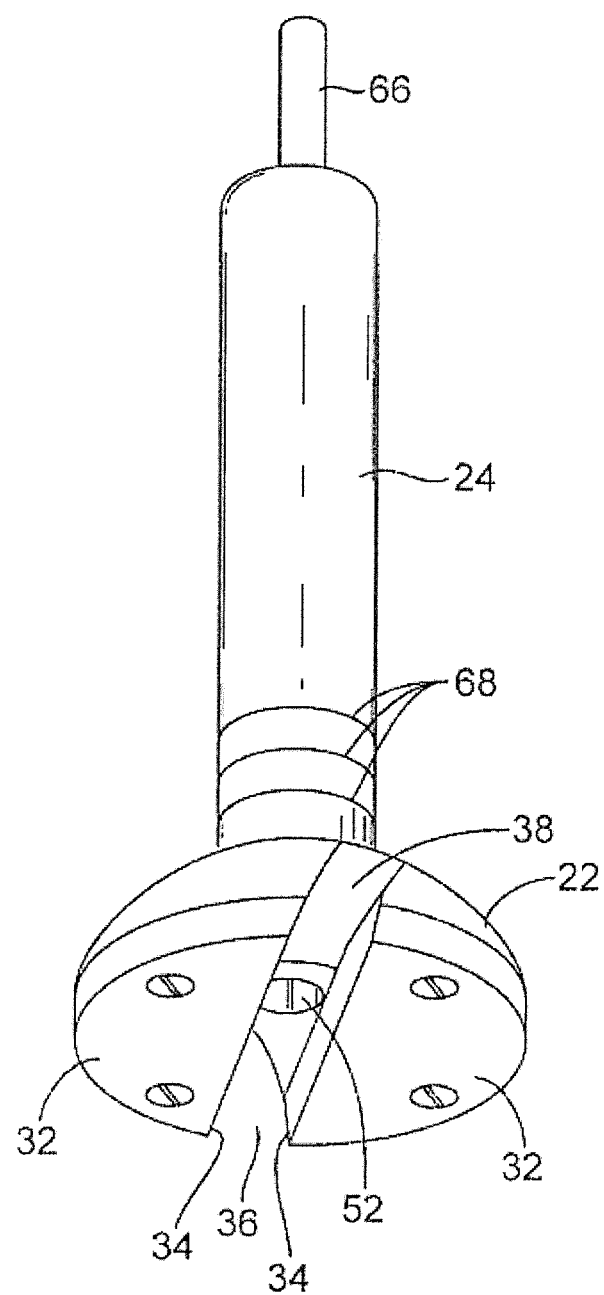
FIG. 7 is a perspective view of a representative embodiment of the milling bit.

Referring now to FIGS. 6 and 7, various perspective views of implementations of the milling bit 20 are shown. Of particular note are the various configurations of removable blades 32. The removable blade 32 is attached to the cutting head portion 22 via a set of screws 110. As such, the blade 32 is easily removed from the bit 20 to allow sharpening and/or replacement of the blade 32. As shown in FIG. 6, some implementations of the removable blade 32 include a single window 36 and a single cutting edge 34. As shown in FIG. 7, some implementations of the removable blade 32 include multiple windows 36 and multiple cutting edges 34.

Figure 8:
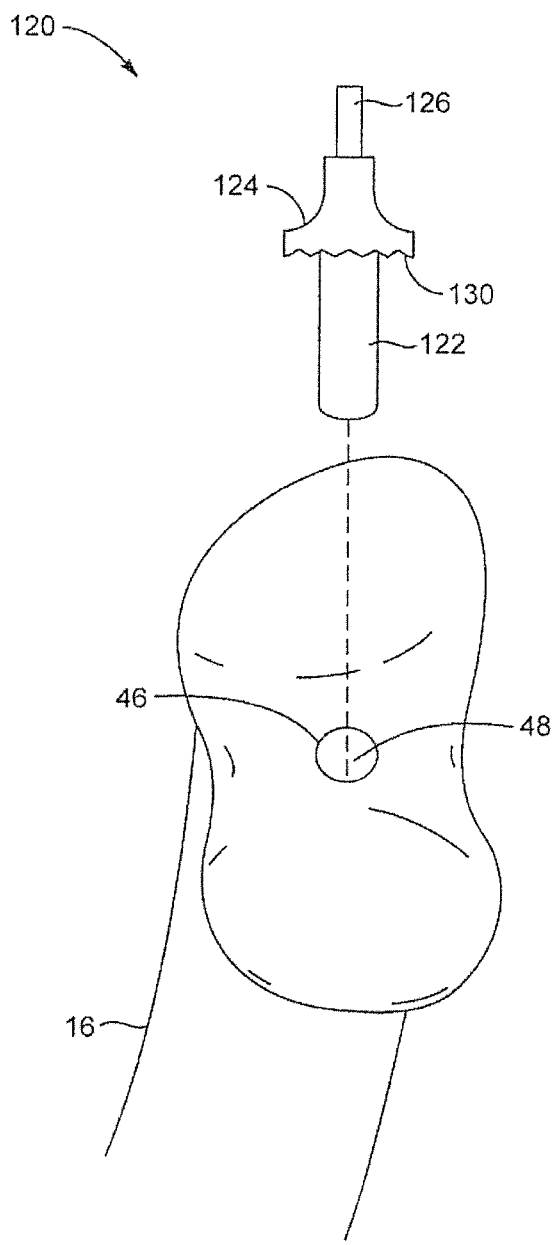
FIG. 8 is a perspective view of a representative embodiment of the bone milling device as embodied in a singular unit.

Referring now to FIG. 8, an implementation of a bone milling device 120 is shown. Unlike the previously discussed bone milling device 10, the present device 120 combines all of the elements of the bone milling device 10 into a singular unit 120. The bone milling device 120 comprises a guide rod 122, a cutting head portion 124, and a shank 126. The guide rod 122 is sized and adapted to rotatably insert within the opening 46 of the bone 16. The guide rod 122 thereby aligns and directs the cutting head portion 124 into the opening 46 of the bone 46. The shank 126, as previously discussed, couples the milling device 120 to a drill (not shown) or other means for rotating the milling device 120.

The cutting head portion 124 includes a plurality of annularly situated cutting teeth 130. Unlike the cutting edge 34 of the previous embodiments, the cutting teeth 130 provide a corrugated surface of sharpened edges that extend radially outward from the guide rod 122. Thus, the cutting teeth 130 contact and grind the adjacent surfaces of the opening 46 to level or knock down any inconsistent features or ridges of the bone 16 surface. As such, the cutting teeth 130 provide a uniform surface having a diameter equal to the diameter of the cutting head portion 124. The milling device 120 is useful where a level and consistent bone surface is required adjacent to the opening 46. In some implementations of the milling device 120, the cutting head portion 124 includes a plurality of cutting edges and windows to form an aperture in the bone 16.

Thus, as discussed herein, the embodiments of the present invention embrace technologies and methods for accurately milling a bone preparatory to an arthroplasty procedure. As will be appreciated by one of skill in the art, the present invention may be embodied in other specific forms without departing from its spirit or essential characteristics. For example, in some embodiments the present invention is modified for use in a unicompartmental knee arthroplasty procedure. In another embodiment, the present invention is modified for use in a total knee arthroplasty procedure. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A cannulated milling assembly for cutting an aperture in a bone, the assembly comprising:
a milling tool member having a cutting head portion and a shank portion, the cutting head portion having a cutting surface disposed at a first end of the shank portion, the shank portion having a cavity with an opening, the cavity extending along a length of the shank portion, the opening being in fluid communication with the cutting head portion and the cutting surface, and the shank portion having a coupling surface at a second end of the shank portion; and
a guide rod having a first portion and a second portion, the first portion being configured to be inserted into the bone so that a part of the second portion extends outwardly from the bone, the second portion being configured to be rotatably inserted within the cavity of the milling tool member, wherein the milling tool member is configured to be rotatable relative to the guide rod so as to be movable into the bone along a longitudinal axis of both the first portion and the second portion of the guide rod to cut the aperture, wherein the longitudinal axis of the guide rod passing through the first portion and the second portion of the guide rod is substantially straight, and wherein the first portion and the second portion of the guide rod are configured to selectively couple to and decouple from each other.

2. The assembly of claim 1, wherein the cutting surface is disposed at a first plane and the shank portion extends outwardly from the cutting head portion in a second plane, the second plane being substantially perpendicular to the first plane, and the cavity being in the second plane.

3. The assembly of claim 1, wherein the cutting surface comprises at least one of: (a) a plurality of annularly situated cutting teeth and (b) a partially disk-shaped object having a cutting edge.

4. The assembly of claim 1, wherein the first portion of the guide rod comprises a first shaft having a first outer diameter, wherein the second portion of the guide rod comprises a second shaft having a second outer diameter that is smaller than the first outer diameter, and wherein the second portion of the guide rod further comprises a third shaft portion having a third outer diameter that is approximately equal in diameter to the first diameter of the first shaft.

5. The assembly of claim 1, wherein the cutting head portion further comprises a bell-shaped portion, wherein the cutting head portion further comprises a recess that extends into the bell-shaped portion, wherein the recess is in fluid communication with the cavity in the shank portion, and wherein the recess has a larger inner diameter than the cavity.

6. The assembly of claim 1, wherein the cutting head comprises at least two windows configured to allow shavings to be removed from the cutting head as the cutting head is used to mill the bone.

7. The assembly of claim 1, wherein the first portion of the guide rod is configured to be selectively separated from the second portion of the guide rod and to be selectively attached with a resection block.

8. The assembly of claim 1, further comprising a resection block having a channel, wherein the second portion of the guide rod is configured to extend through the channel to guide placement of the resection block with respect to the bone.

9. The assembly of claim 4, wherein the cutting head portion comprises a recess in fluid communication with the cavity, wherein the recess has a larger inner diameter than the cavity, the recess being structured to receive the third portion of the guide rod having the third diameter such that a part of the third portion is extended into the recess.

10. The assembly of claim 1, further comprising a depth gauge having an arm that extends laterally from the shank portion, wherein the depth gauge is configured to indicate a depth to which the milling tool has moved into the bone.

11. The assembly of claim 1, wherein an outer surface of the shank portion further comprises a plurality of annular reference marks.

12. The assembly of claim 1, wherein the first portion of the guide rod comprises a set of threads into which a plurality of surgical instruments is threadable, one of which is the second portion of the guide rod.

13. The assembly of claim 1, further comprising a resection block that is configured to attach to the guide rode when the milling tool is removed from the second portion of the guide rod, and wherein the resection block comprises a cutting tool guide that is configured to guide a cutting tool to cut the bone to a depth of the aperture.

14. A cannulated milling assembly for cutting an aperture in a bone, the assembly comprising:
a milling tool member having a cutting head portion and a shank portion, the cutting head portion having a cutting surface disposed at a first end of the shank portion, the shank portion defining a cavity with an opening, the cavity extending within a length of the shank portion, the opening being in fluid communication with the cutting head portion, and the shank portion having a coupling surface at a second end of the shank portion;
a guide rod having a first portion and a second portion, the first portion being configured to be inserted into the bone so that a part of the second portion extends outwardly from the bone, the second portion being configured to be rotatably inserted within the cavity of the milling tool member, wherein the milling tool member is configured to be rotatable relative to the guide rod so as to be movable into the bone along a longitudinal axis of both the first portion and the second portion of the guide rod to cut the aperture; and
a depth gauge comprising a coupling surface, wherein the milling tool is configured to be coupled with the coupling surface such that the milling tool is rotatable with respect to the depth gauge, and wherein the depth gauge is configured to indicate the depth of the cutting head portion of the milling tool member in the bone.

15. The assembly of claim 14, wherein a longitudinal axis passing through a length of the first portion and a length of the second portion of the guide rod is substantially straight, wherein the first portion of the guide rod comprises a first shaft having a first outer diameter, and wherein the second portion of the guide rod comprises a second shaft having a second outer diameter that is smaller than the first outer diameter.

16. The assembly of claim 15, wherein the second portion of the guide rod further comprises a third shaft portion having a third outer diameter that is approximately equal in diameter to the first diameter of the first shaft.

17. The assembly of claim 16, wherein the first portion and the second portion are configured to selectively couple to and decouple from each other.

18. A cannulated milling assembly for cutting an aperture in a bone, the assembly comprising:
a milling tool member having a cutting head portion and a shank portion, the cutting head portion having a cutting surface at a first end of the milling tool, with the shank portion extending outwardly from the cutting head, the shank portion having a cavity with an opening, the cavity extending along a length of the shank portion, the opening being in fluid communication with the cutting head portion, the shank portion having a coupling surface at a second end of the milling tool, and the cutting portion defining a recess having a larger diameter than the cavity in of the shank portion; and
a guide rod having a first portion and a second portion, the first portion being configured to be inserted into the bone so that the second portion extends outwardly from the bone, the second portion being configured to be rotatably inserted within the cavity of the milling tool member, wherein the milling tool member is configured to be rotatable relative to the guide rod so as to be movable into the bone along a longitudinal axis of the first and second portions of the guide rod to cut the aperture, wherein the first portion of the guide rod comprises a first diameter and the second portion of the guide rod comprises a second diameter that is smaller than the first diameter, wherein the recess in the cutting head portion is sized to receive the first portion of the guide rod that comprises the first diameter, wherein the cavity in the shank portion is sized to receive the second portion of the guide rod that comprises the second diameter, while preventing the first portion of the guide rod that comprises the first diameter from being inserted into the cavity, and wherein the milling tool is configured to remove bone from the first diameter of the first portion of the guide rod to an outer perimeter of a face of the cutting head portion.

19. The assembly of claim 18, further comprising a depth gauge comprising a coupling surface, wherein the milling tool is configured to be coupled with the coupling surface such that the milling tool is rotatable with respect to the depth gauge, and wherein the depth gauge is configured to indicate the depth of the cutting head portion of the milling tool in the bone.

20. The assembly of claim 18, wherein the first portion and the second portion are selectively coupleable to and decoupleable from each other, and wherein the longitudinal axis of both the first portion and the second portion of the guide rod is substantially straight.

* * * * *